United States Patent
Van Blitterswijk et al.

(10) Patent No.: US 6,299,650 B1
(45) Date of Patent: *Oct. 9, 2001

(54) METHOD FOR IN VITRO PRODUCTION OF BONE

(75) Inventors: Clemens Antoni Van Blitterswijk, Hekendorp; Joost Dick De Bruijn; Yvonne Pearl Bovell, both of Den Haag, all of (NL)

(73) Assignee: IsoTis N.V., Bilthoven (NL)

(*) Notice: Subject to any disclaimer, the term of this patent is extended or adjusted under 35 U.S.C. 154(b) by 0 days.

This patent is subject to a terminal disclaimer.

(21) Appl. No.: 09/621,178

(22) Filed: Jul. 21, 2000

Related U.S. Application Data

(63) Continuation of application No. 08/810,266, filed on Mar. 3, 1997, now Pat. No. 6,152,964.

(30) Foreign Application Priority Data

Mar. 3, 1996 (EP) .................................. 96200553
Sep. 11, 1996 (EP) .................................. 96202536

(51) Int. Cl.$^7$ .................................. A61F 2/36
(52) U.S. Cl. .................. 623/23.63; 623/23.72; 623/16.11; 435/372; 435/377
(58) Field of Search .................. 623/23.63, 23.72; 435/372, 384

(56) References Cited

U.S. PATENT DOCUMENTS

| 4,963,489 | 10/1990 | Naughton et al. | ............ 435/240.1 |
|---|---|---|---|
| 5,522,895 | 6/1996 | Mikos | ............ 623/16 |
| 5,908,784 | 6/1999 | Johnstone et al. | ............ 435/372 |
| 5,972,703 | 10/1999 | Long et al. | ............ 435/372 |

FOREIGN PATENT DOCUMENTS

| 7-194373 | 8/1995 | (JP) . |
|---|---|---|
| WO 92/10563 | 6/1992 | (WO) . |
| WO 95/03011 | 2/1995 | (WO) . |

OTHER PUBLICATIONS

Puleo et al., "Osteoblast responses to orthopedic implant material in vitro," *J. Biomed. Mat. Res.*, 25:711–723 (1991).

Radder et al., "Bone–bonding behaviour of poly(ethylene oxide)–polybutylene terephthalate copolymer coatings and bulk implants: a comparative study," *Biomaterials*, 16(7):507–513 (1995).

*Primary Examiner*—Dinh X. Nguyen
*Assistant Examiner*—Thomas Barrett
(74) *Attorney, Agent, or Firm*—Banner & Witcoff, Ltd.

(57) ABSTRACT

The invention relates to a method for in vitro production of bone tissue, comprising the steps of:

(a) applying undifferentiated mammalian cells, in particular autologous marrow cells, on a substrate;

(b) directly contacting said cells with a culture medium for a sufficient time to produce a continuous matrix;

(c) removing the substrate with the matrix from the culture medium.

The produced matrix can be used for joint prostheses, maxillofacial implants, special surgery devices, or bone fillers. The contacted culture medium can also be used for the production of active factors such as growth factors.

17 Claims, 4 Drawing Sheets

METHOD FOR IN VITRO PRODUCTION OF BONE

This is a continuation of application U.S. Ser. No. 08/810,266, filed Mar. 3, 1997 now U.S. Pat. No. 6,152,964.

The invention relates to a method of producing bone tissue in vitro on a substrate, which can be used as a bone implant.

BACKGROUND

U.S. Pat. No. 5,306,305 (=WO 95/19152) discloses an in vitro method for producing an implant device by coating a gel containing osteoblast cells onto a porous metal surface and then incubating the gel in a growth medium. A repeatedly renewed minimal essential medium (MEM) is used for about 3 weeks for cell multiplication, followed by a medium containing β-glycerophosphate and ascorbic acid for another 1–2 weeks. The cells may originate from the patient's own bone fragments. The gel (e.g. 0.5% gelatin) is used to hold the cells to the substrate surface.

DE-A-3810803 discloses a method of producing living bone substitute materials by in vitro culturing autologous bone cells from human bone fragments in a repeatedly renewed culture medium, followed by deposition of the cultured cells in a porous calcium phosphate matrix and additional culturing. The composite material can be reimplanted.

WO 94/04657 discloses a bioactive porous glass which is pretreated in such a way that it cannot raise the pH of a tissue medium contacted with the glass. It also reports the seeding of the pretreated porous glass with osteoblasts.

These prior art methods of in vitro production of bone tissue for implanting purposes have not yet been put into practice, probably because fixation of the resulting implant in the body and thus functioning of the implant are insufficient due to limitations in the applying techniques. No biological effect of using a particular culture method was described in the prior art. Furthermore, these prior methods necessitate the introduction of a bone defect (a lesion) in the patient in order to obtain the required bone cells.

SUMMARY OF THE INVENTION

It has been found now that these drawbacks can be overcome by a method wherein, instead of differentiated bone cells such as osteoblasts, undifferentiated cells are used for covering the implant substrate, and said cells are incubated with a liquid culture medium.

Consequently, the present invention concerns, in a first aspect, a method for in vitro production of bone tissue, comprising the steps of:

(a) applying undifferentiated mammalian cells on a substrate;

(b) directly contacting said cells with a culture medium for a sufficient time to produce a mineralised or non-mineralised matrix;

(c) removing the substrate with the matrix from the culture medium.

DETAILED DESCRIPTION OF THE INVENTION

The invention provides a method for producing a substrate with a matrix grown thereon, which can be used preferably for the provision of load-bearing implants, including joint prostheses, such as artificial hip joints, knee joints and finger joints, and maxillofacial implants, such as dental implants. It can also be used for special surgery devices, such as spacers, or bone fillers, e.g. for use in augmentation, obliteration or reconstitution of bone defects and damaged or lost bone. Bone formation can be optimised by variation in mineralisation, both by inductive and by conductive processes. A combination of the provision of a load-bearing implant (preferably coated with a matrix as described above) with a bone filler comprising a matrix as described, constitutes an advantageous method according to the invention.

The method of the invention is also very suitable in relation to revision surgery, i.e. when previous surgical devices have to replaced.

Undifferentiated cells are pluripotent cells which are in an early stage of specialisation, i.e. which do not yet have their final function and are still in the process of proliferation. In particular these are cells which have not yet differentiated to e.g. osteoblasts or osteoclasts. Such cells are especially blood cells and cells present in bone marrow. Especially suitable undifferentiated cells are bone marrow cells, including haematopoietic cells and in particular stromal cells. The marrow cells, and especially the stromal cells were found to be very effective in the bone producing process when taken from their original environment.

The undifferentiated cells can be directly applied on the substrate in step (a) or they can advantageously be multiplied in the absence of the substrate before being applied on the substrate. In the latter mode, the cells are still largely undifferentiated after multiplication and, for the purpose of the invention, they are still referred to as undifferentiated. During step (b) the cells are allowed to differentiate. Differentiation can be induced or enhanced by the presence of suitable inductors, such as glucocorticoids, e.g. dexamethasone.

The use of undifferentiated cells provides several advantages. Firstly, their lower differentiation implies a higher proliferation rate and allows the eventual functionality to be better directed and controlled. Moreover, culturing these cells not only produces the required bone matrix containing organic and inorganic components, but also results in the presence, in the culture medium and in the matrix, of several factors which are essential for growth of the tissue and for adaptation to existing living tissue. Also, the culture medium can be a source of active factors such as growth factors, to be used in connection with the implanting process. Furthermore, such undifferentiated cells are often available in larger quantities and more conveniently than e.g. mature bone cells, and exhibit a lower morbidity during recovery. Matrices as thick as 100 μm can be produced as a result of the use of undifferentiated cells.

The cells to be used can be allogeneous cells, but it will often be preferred to use cells originating from the same subject for which the implant is intended, i.e. autologous cells.

The substrate on which the undifferentiated cells can be applied and cultured can be a metal, such as titanium, cobalt/chromium alloy or stainless steel, a bioactive surface such as calcium phosphate, polymer surfaces such as polyethylene, and the like. Although less preferred, siliceous material such as glass ceramics, can also be used as a substrate. Most preferred are metals, such as titanium, and calcium phosphates, even though calcium phosphate is not an indispensable component of the substrate. The substrate may be porous or non-porous.

The cells can be applied at a rate of e.g. $10^3$–$10^6$ per cm$^2$, in particular $10^4$–$2.10^5$ cells per cm$^2$.

The culture medium to be used in step (b) of the method according to the invention can be a commonly known culture medium such as MEM (minimum essential medium). Advantageously, the medium can be a conditioned medium. In this context, a conditioned medium is understood to be a medium wherein similar cells have previously been incubated, causing the medium to contain factors which are important for cell growth and cell differentiation.

The cells are cultured for a time to produce a sufficient matrix layer, e.g. a matrix layer having a thickness of at least 0.5 μm, in particular from 1 up to 100 μm, more in particular of 10–50 μm. The cells may be contacted with the culture medium for e.g. 2–15 weeks, in particular 4–10 weeks.

The production of the matrix, when applied on a substrate, results in a continuous or quasi-continuous coating covering the substrate for at least 50%, in particular at least 80% of its surface area.

The invention also pertains to a method of producing active factors such as growth factors, comprising the steps of:

(a) applying undifferentiated mammalian cells, especially marrow cells, more in particular stromal cells on a substrate;

(b) directly contacting said cells with a culture medium for a sufficient time to produce growth factors;

(c) removing the substrate with the matrix from the culture medium;

(d) recovering the active factors from the culture medium.

The cells applied in step (a) may be undifferentiated cells directly applied as such, or they may be cells that, prior to step (a), have been multiplied in a culture medium without the substrate.

These active factors comprise growth factors and other substances which are involved in bone formation and remodelling, cell proliferation and cell adhesion. These factors can advantageously be used in conjunction with an implant procedure, whereby the active factors, possibly together with other components of the culture medium, are administered to the patient in order to enhance the functioning and adaptation of the implant. The use of autologous cells is preferred in this procedure.

The method of the invention can be carried out following the principles and procedures as described in the following general examples.

The invention also comprises a method of restoring a load-bearing structure in a mammal, including man, comprising introducing into the mammalian subject a substrate coated with a continuous matrix produced as described above as an implant into the site of the structure to be restored. The structure to be restored is in particular a joint structure or mandible (tooth) structure. This method also applies to prostheses and to revision surgery. The method can be combined with introducing a bone filler obtained by the method described above.

EXAMPLES

Example 1

Rat bone marrow cell (RBMC) culture technique

The rat bone marrow technique allows the production of a bone-like mineralised matrix on various substrata.

In brief, bone marrow cells are isolated from the femora of young adult male rats and are cultured for up to 4 weeks, in order to produce bone-like tissue. The culture medium used comprises α-minimal essential medium supplemented with foetal calf serum, antibiotics, ascorbic acid, β-glycerophosphate and dexamethasone. In this system, the latter three components are essential for the production of bone-like tissue. Ascorbic acid is required for collagen synthesis and for osteogenesis in vitro. Furthermore, it has been demonstrated that ascorbic acid regulates ATPase and alkaline phosphatase activities and protein synthesis in cultures of osteoblast-like cells. β-Glycerophosphate is used as a source of organic phosphate ions, which is therefore important for mineralisation. If no β-glycerophosphate is added a largely non-mineralised matrix is obtained. Dexamethasone, a synthetic glucocorticoid, induces proliferation and terminal differentiation of osteogenic cells.

From approximately 2 weeks onwards, opaque, three dimensional mineralised nodular structures develop. These nodules can be identified macroscopically and become denser, larger and more opaque with time.

SEM observations show the presence of mineralised collagen fibres, in association with globular structures deposited on the surface of the substrata. The globular structures are approximately 0.2–1 μm in diameter and have been shown to be mineralised and contain bone-specific proteins (e.g. osteopontin). The result is shown in FIG. 1.

The osteogenic character of the rat bone marrow culture system has been well characterised using a number of criteria as outlined below:

(i) The cellular and extracellular matrix in the nodules have similar morphological and ultrastructural characteristics to bone tissue.

(ii) Cells associated with these nodules stain intensely for the enzyme alkaline phosphatase, which is a characteristic of osteoblastic cells.

(iii) The nodules are Von Kossa (phosphate) and alizarin red (calcium) positive.

(iv) The CaP globules fuse to form a cement line that is rich in glycosaminoglycans.

(v) Collagen fibres have a periodicity of 64–67 nm, resembling collagen type I that is also present in bone.

(vi) Ultrastructurally, mineralisation is composed of needle-shaped bone-like crystals.

(vii) X-ray microanalysis (XRMA) shows the presence of Ca and P (see FIG. 2).

(viii) During time, the cultures express a peak alkaline phosphatase/DNA ratio at around day 12, which is characteristic for rat osteogenic cultures.

(ix) Osteocalcin (bone protein) production has been shown to commence at day 4 (see FIG. 3).

Summarising, based on both morphological and immunohisto/cyto-chemical data, the osteogenic character of the technique has been demonstrated.

Example 2

Human bone marrow culture (HBMC) technique

Human bone marrow cells can be cultured under similar conditions to those described for the rat bone marrow culture technique. Instead of using foetal calf serum in the culture medium the use of autologous serum (from the donor patient) or synthetic serum is equally possible. To date, characterisation has also demonstrated the osteogenic capacity of this culture system, as outlined below:

After approximately 4 weeks, 'nodules' develop which are more widespread and less distinct than those seen in a standard RBMC culture.

SEM observations show the presence of mineralised collagen fibres, and globular structures deposited on the surface of the substrata. The globular structures are approximately 1–2 µm in diameter and resemble the calcium phosphate globules seen in rat bone marrow cultures (although they are somewhat larger than seen in the RBMC culture). In general, the globular layer is abundant and is also seen in association with mineralised collagen fibres. The result is shown in FIG. 4.

Similar to the RBMC cultures, these nodules stain positively for alkaline phosphatase, calcium and phosphate.

During time, the cultures express a peak alkaline phosphatase/DNA ratio at around day 20, this later expression correlates with the delayed onset of mineralisation in the HBMC.

Example 3

Osteoclast cultures on calcium phosphates (CaP) substrata

Objective

The objective of this study was to examine the influence of osteoblast derived factors on osteoclastic resorption.

Materials and methods

Experimental set-up: The cultures were divided into 2 groups: (i) CaP with osteoclasts only and (ii) CaP with osteoblasts, followed by osteoclasts.

Preparation of calcium phosphate samples: All calcium phosphate samples were polished to give a similar surface roughness and were cleaned and sterilised prior to use.

Osteoblast cultures: Bone marrow cells were isolated from young rats as follows: The femora were dissected, washed well and the epiphyses removed. The bone marrow was subsequently flushed out of the marrow cavity using a syringe, with attached hypodermic needle, filled with alpha-minimum essential medium supplemented with 15% foetal bovine serum, antibiotics, 50 µg/ml ascorbic acid, $10^{-8}$ M dexamethasone and 1 M β-glycerophosphate. The cell suspension was then seeded onto the samples and was cultured for 18 days.

Osteoclast cultures: Bone marrow cells were isolated from the femora of young rats as described above, in medium without dexamethasone added.

Fixation: Following the culture period, the wells were washed 3 times in PBS at 37° C. followed by fixation in 2% paraformaldehyde/2.5% glutaraldehyde in 0.1 M sodium cacodylate buffer, pH 7.4, at 4° C. Subsequently, they were washed in distilled water, prior to TRAP staining.

Tartrate resistant acid phosphatase (TRAP): Tartrate resistant acid phosphatase was detected using a modification of the azo-dye method described by Barka (1), in which 3.9 mg/ml tartaric acid was added to the incubation solution. Following staining, the samples were washed well in distilled water, and where possible, the cell multilayer was removed; this facilitated visualisation of the TRAP +ve cells. The samples were subsequently prepared for scanning electron microscopy.

Scanning electron microscopy: Samples were dehydrated through a graded ethanol series and critical point dried from $CO_2$. All samples were sputter-coated with gold prior to examination.

Results

Osteoclast cultures: Osteoclasts (TRAP positive cells) were seen on the different materials, although resorption of the underlying substrates was not observed.

Osteoblast- followed by osteoclast-cultures: Osteoclasts were present on the materials and resorption of the mineralised matrix formed by the osteoblasts was seen. In the case of hydroxyapatite sintered at 600° C. and tricalcium phosphate (TCP), resorption of the underlying substrates was also observed.

Conclusions

This example demonstrates that osteoclasts are capable of resorbing certain calcium phosphates, but only when osteoblasts are firstly cultured on the substrates. This suggests a conditioning of the substrate surfaces, by factors produced by osteoblasts, that have a stimulating effect on osteoclastic activity.

Example 4

Osteoclast cultures on apatite pre-treated with osteoblast conditioned medium

Objective

The objective of this experiment was to investigate the effect of osteoblast conditioned medium on osteoclastic resorption of an apatite layer. Following the culture period, the number of tartrate resistant acid phosphatase positive cells (osteoclasts) were quantified and the samples were examined to see whether osteoclastic resorption of the apatite layer had occurred.

Materials and methods

Pretreatment of an apatite layer with conditioned or control medium: Sterile samples were incubated in osteoblast conditioned medium for approximately 16 hours, prior to the osteoclast culture. Control samples were also incubated in non-conditioned medium (alpha-minimum essential medium) for 16 hours.

Osteoclast culture: A neonate chick osteoclast culture was performed on both sets of samples. The osteoclasts were cultured in alpha-minimum essential medium supplemented with 10% FCS and $10^{-6}$ M $PGE_2$ (prostaglandin $E_2$) for 48 hours at 37° C.

Fixation: Following the culture period, the wells were washed 3 times in PBS at 37° C., followed by fixation in 1.5 glutaraldehyde in 0.14M sodium cacodylate buffer, pH 7.4, at 4° C. for 15–30 minutes. Subsequently, they were washed in distilled water, prior to TRAP staining.

Tartrate resistant acid phosphatase (TRAP) was detected using a modification of the azo-dye method described by Barka (1), in which 3.9 mg/ml tartaric acid was added to the incubation solution. Following staining, the samples were washed well in distilled water and, where possible, the cell multilayer was removed; this facilitated visualisation of the TRAP +ve cells. Photomicrographs were then made and the samples were subsequently prepared for scanning electron microscopy.

Scanning electron microscopy: The samples were dehydrated through a graded ethanol series and critical point dried from $CO_2$. All samples were sputter-coated with gold prior to examination.

Results

Using reflected light microscopy, TRAP positive cells were observed both on the treated and control samples; the number of TRAP positive cells were counted, the results for the conditioned medium being about 220 and for the non-conditioned control medium being about 25.

Using scanning electron microscopy, resorption of the apatite was clearly seen on both the treated and control samples. Although the number of resorption lacunae were not quantified, there was an impression that there were more present on the samples treated with conditioned medium.

Conclusions

This experiment has demonstrated that there is a significant increase in the number of osteoclasts on the apatite layer following pretreatment with osteoblast conditioned medium (see FIG. 5). This difference suggests the presence of an osteoclast stimulating factor, produced by osteoblasts, in the conditioned medium.

Example 5

Implantation of a composite of porous hydroxyapatite and cultured rat bone marrow cells Introduction Fischer 344 rat bone marrow cells cultured on a porous hydroxyapatite substrate were implanted subcutaneously into other Fischer 344 individuals. The purpose of this study was to assess the osteoconductive and osteoinductive capacity of the obtained composite.

Materials and methods

Hydroxyapatite discs: porous hydroxyapatite blocks (8*2*2 mm) sintered at 1300° C. for 96 h.

Rats: Implantation into 7 weeks old male albino Fischer rats (about 250–300 g).

Culture protocol: Rat bone marrow cells were cultured on and in the hydroxyapatite discs for four weeks according to the method described earlier. Rat bone marrow cells were isolated and transferred to 75 m² flasks and cultured (estimated gain $1.5*10^6$ cells per flask). After 7 days the cells were trypsinised, counted and seeded on the hydroxyapatite and the controls at $1-2*10^5$ cells per cm². In the constructs cells were cultured for 4 weeks prior to implantation.

Implantation procedure: The constructs were implanted subcutaneously into the back of the rats. After 4 weeks of implantation the animals were killed and the samples were fixed in glutaraldehyde.

Evaluation procedure: The samples were dehydrated to ethanol 100% and then embedded in methyl methacrylate solution or critical point dried. The samples were examined by light microscopy or back-scattered and regular electron microscopy.

Controls: As controls hydroxyapatite blocks were used that were incubated in tissue culture medium for four weeks without cells which were then implanted similar to the constructs. Also cells were cultured on the hydroxyapatite blocks for a period of 8 weeks and not implanted into rats.

Results

It was noted that after 4 weeks of tissue culture in the hydroxyapatite blocks matrix had been formed by the cells on the surface of the construct and in its pores. Part of the matrix was calcified. After 8 weeks of culture this matrix formation was more prominent and ca. 50 μm thick matrices were obtained, furthermore, calcification was more extensive. Hydroxyapatite blocks that had not been incubated with cultured cells showed no matrix formation.

After 4 weeks of implantation the control hydroxyapatite blocks (without cultured cells) showed no bone formation on their surface. Only fibrous tissue and exudate could be observed. The situation for the constructs (with cultured cells and matrix) was substantially different. Especially in the pores clear signs of bone formation could be observed. This bone formation was clearly distinct from the matrix formation as observed in culture both as far as the 4 weeks and 8 weeks culture period was concerned. Bone formation occurred according to the bonding osteogenesis theory, indicating the osteoconductive nature of the cultured matrix.

Example 6

Osteoblast cultures on in vitro formed mineralised extracellular matrix

The objective of this experiment was to examine the effect of in vitro formed extracellular matrix of the alkaline phosphatase activity of cultured osteoblasts.

Materials and Method

Preparation of cell suspensions: Bone marrow cells were isolated from the femora of young adult Fischer rats and were cultured until near confluency (approximately 7 days), in a-Minimum Essential Medium containing 15% foetal bovine serum, antibiotics, 10 mM β-glycerophosphate, 50 μg/ml ascorbic acid and $10^{-8}$ M dexamethasone. The cells were then briefly rinsed in sterile phosphate buffered saline and were treated with 0.25% trypsin to detach the cells from the culture surface. The cell suspension were pooled and counted in a Burker-Turk haemocytometer.

Stage 1: The cells for the first stage of the experiment were isolated and prepared as described above. The cells were seeded into 12 well tissue culture plates at a density of $1 \times 10^4$ cells/cm² and were cultured in similar medium for 4 weeks, in order to produce a mineralised extracellular matrix. The medium was refreshed three times weekly. Following initial culture period, all wells were rinsed three times with sterile PBS and were then stored at −20° C. for at least 24 hours (in order to kill the cell population), until required for the second stage of the experiment.

Stage 2: The cells for the first stage of the experiment were isolated and prepared as described above and were then seeded as follows:

(i) 12 well plates with in vitro formed extracellular matrix, n=6 (plates prepared in stage 1). The plates with matrix were removed from −20° C. storage, warmed to room temperature, rinsed three times with sterile phosphate buffered saline and finally with a-MEM. The cells were then seed at a density of $1 \times 10^4$ cells/cm² and were cultured for 1, 4, 6, 8, 11, 12, 13, 14 and 15 days. As a control, one plate with matrix was cultured for 15 days in medium only (i.e. without cells).

(ii) Control 12 well tissue culture polystyrene plates, without matrix, n=6. The cells were seeded at a density of $1 \times 10^4$ cells/cm² and were cultured for 1, 4, 6, 8, 11, 12, 13, 14 and 15 days.

At each time period, one plate from each culture group was rinsed in PBS and stored at −20° C. for at least 24 hours. At end of the culture period, all plates were assayed for DNA and alkaline phosphatase activity (APA) analysis. The APA/DNA ratio was then calculated and illustrated graphically.

Results

In stage 1 of this experiment, an abundant mineralised extracellular matrix was formed in all wells after 4 weeks of culture. Abundant mineralised extracellular matrix was also formed in stage 2, but it was not possible to morphologically assess whether there was a difference between the two experimental groups. However, DNA and alkaline phosphatase analysis revealed a clear difference. DNA analysis showed similar cell numbers for both groups (FIG. 6a) whereas the alkaline phosphatase activity was significantly higher for the cells cultured on the in vitro formed extracellular matrix (FIG. 6b). For both groups, the peak alkaline phosphatase activity per cell was seen at day 11, although a significantly higher activity was seen in the presence of the in vitro formed extracellular matrix (FIG. 6c).

Conclusion

Bone marrow cells cultured on an in vitro produced bone matrix have a significantly higher activity than those cultured on tissue culture polystyrene. The presence of this matrix can therefore trigger the activity of, and bone production by osteogenic cells.

Figure 1:
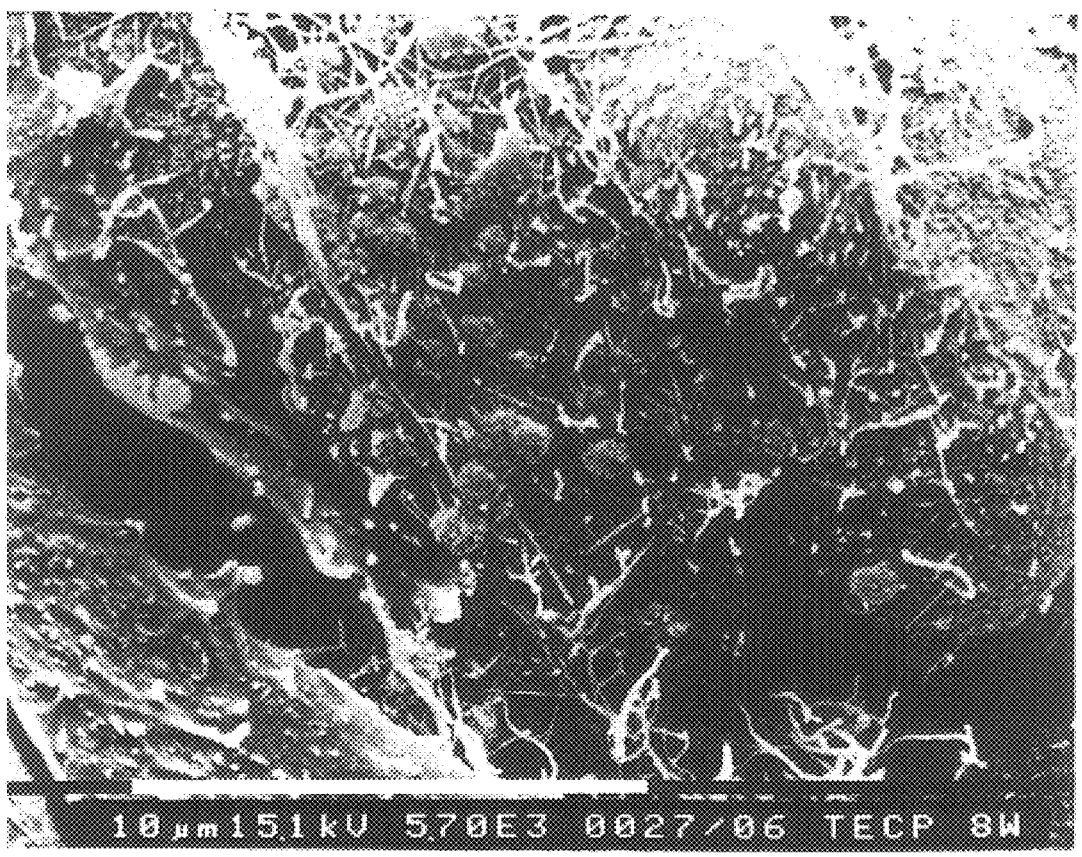
FIG. 1 shows an SEM photograph of in vitro formed bone composed of Ca-P globules and collagen (rat bone marrow culture).
Figure 2:
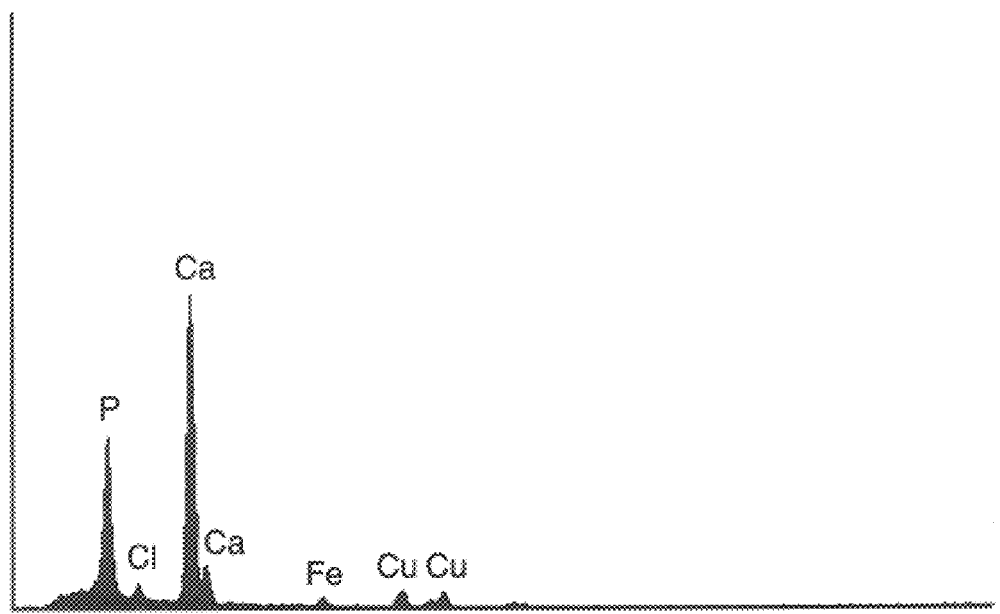
FIG. 2 shows an X-ray microanalysis of the bone marrow culture: P indicates phosphorus and CA indicates calcium; the minor elements originate from the measuring device.
Figure 3:
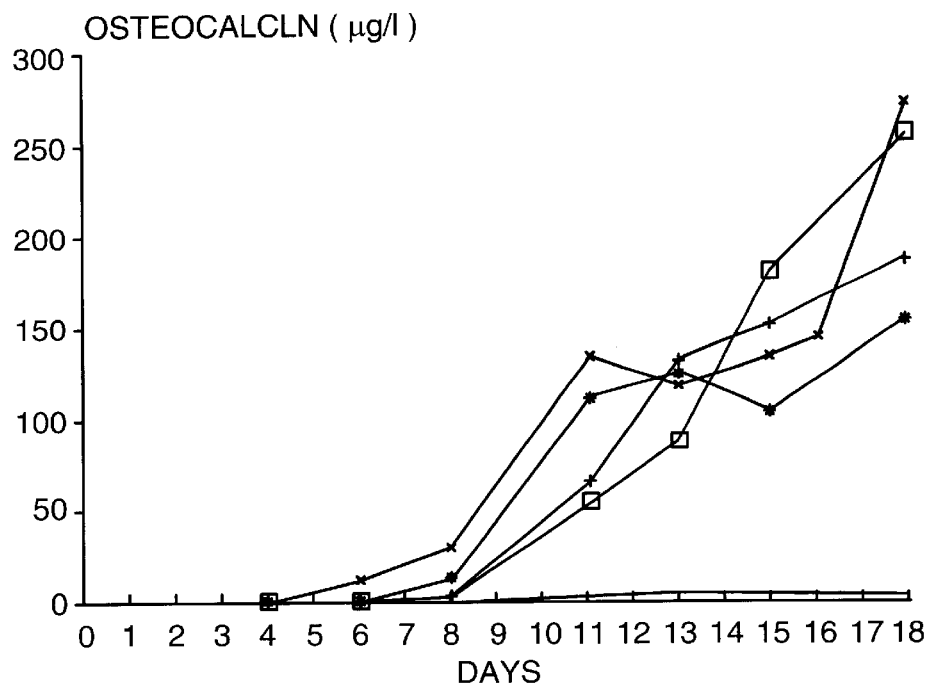
FIG. 3 is a graphical representation of osteocalcin release over time into culture medium from various crystalline hydroxyapatite substrata.
Figure 5:
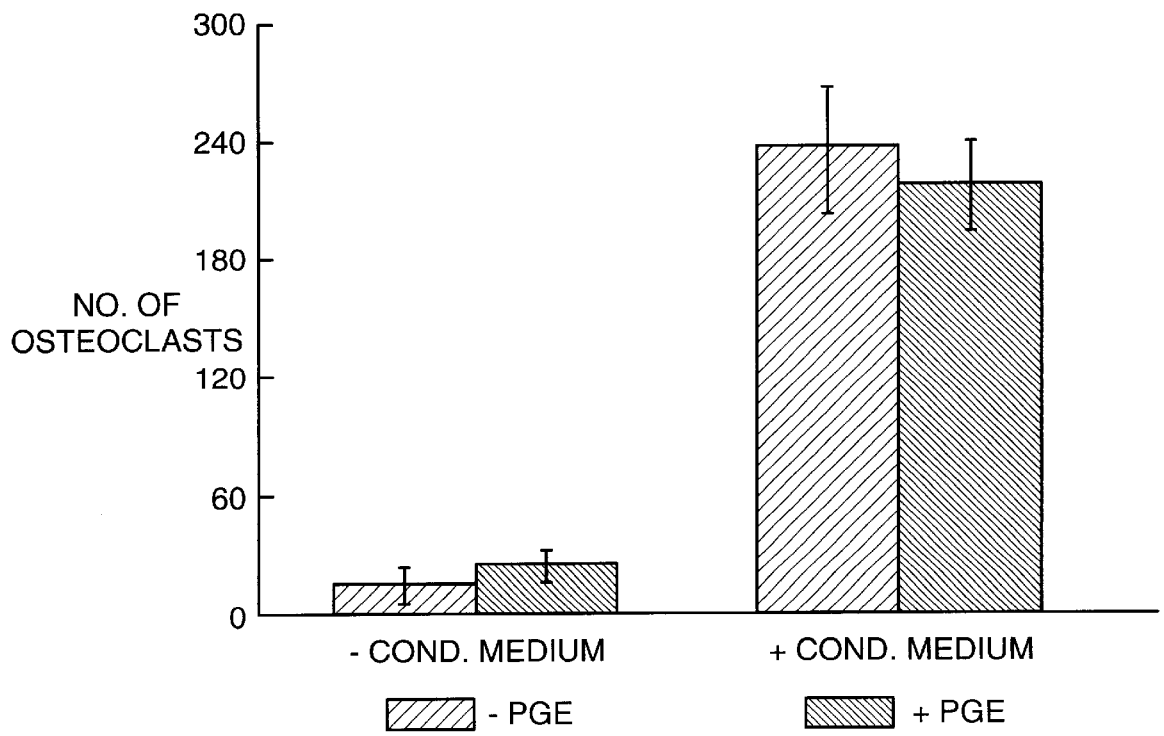
FIG. 5 graphically represents the number of osteoclasts on apatite substrata with and without conditioned medium, with and without $PGE_2$.
Figure 4:
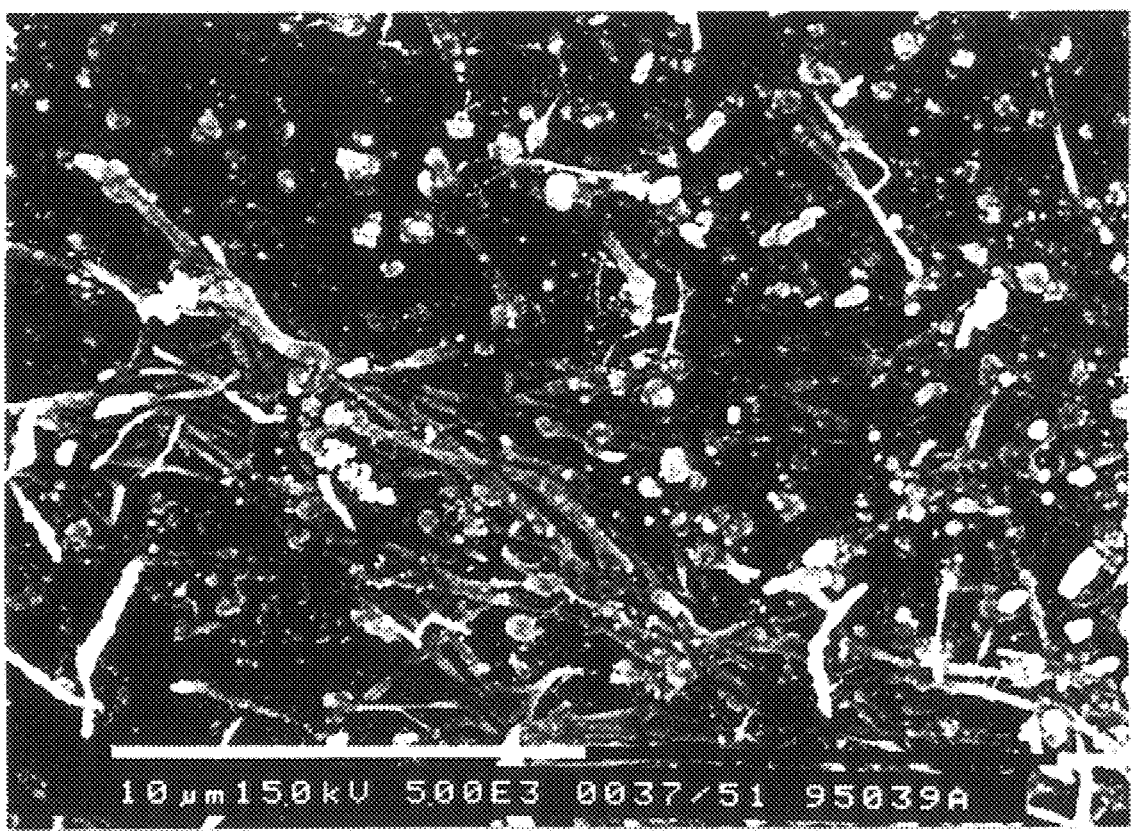
FIG. 4 shows an SEM photograph of in vitro formed bone composed of Ca-P globules and collagen (human bone marrow culture).
Figure 6A:
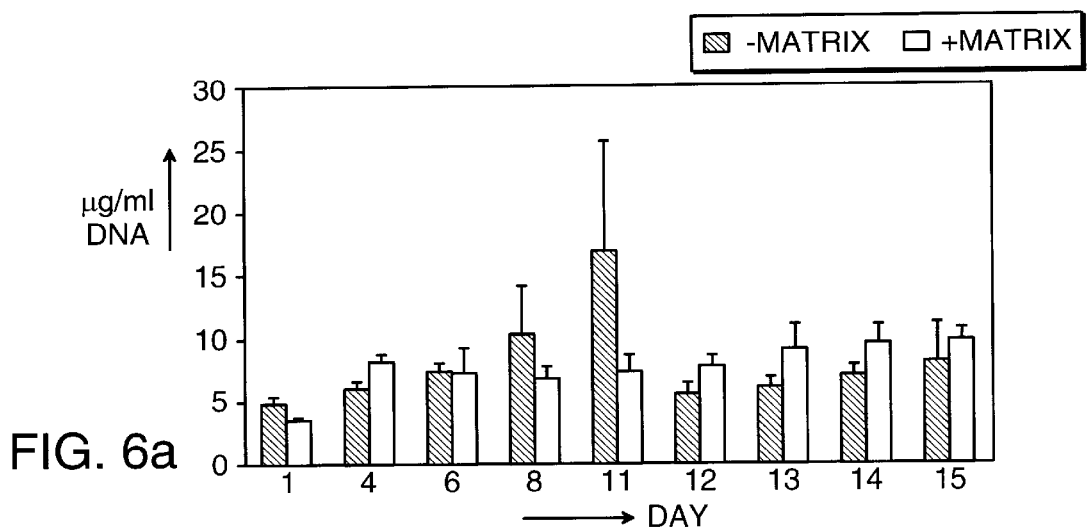
FIG. 6a is a graph showing the DNA content (no. of cells) of a bone marrow cell culture on tissue culture polystyrene (−matrix) and in vitro formed bone matrix (+matrix).
Figure 6B:
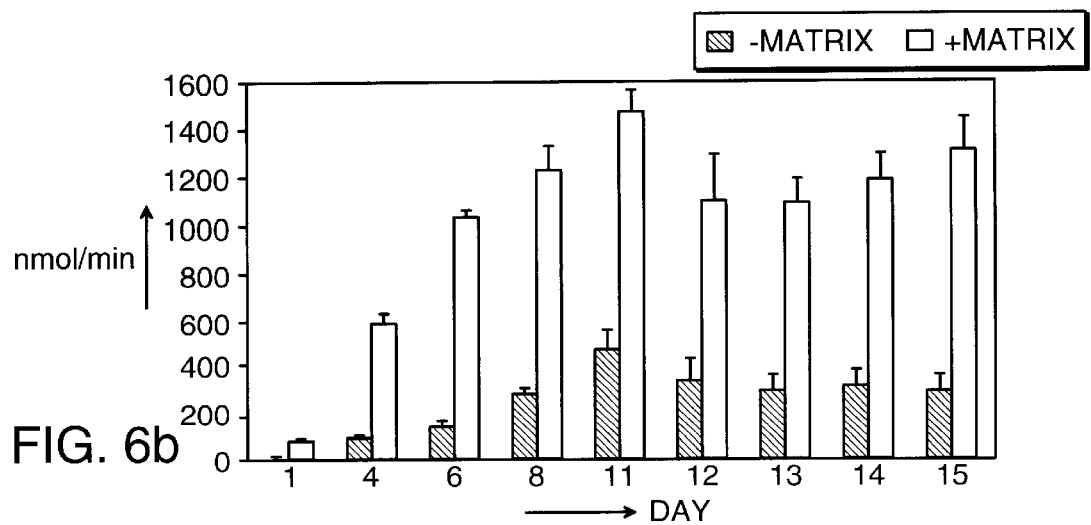
FIG. 6b is a graph showing the alkaline phosphatase activity (APA) of a bone marrow cell culture on tissue culture polystyrene (−matrix) and in vitro formed bone matrix (+matrix).
Figure 6C:
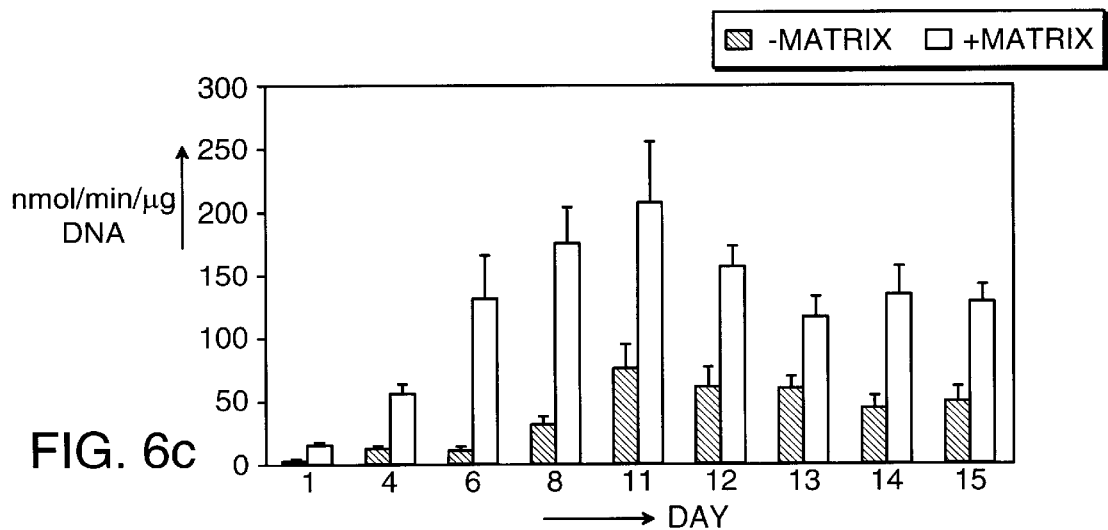
FIG. 6c is a graph showing the APA/DNA ratio of a bone marrow cell culture on tissue culture polystyrene (−matrix) and in vitro formed bone matrix (+matrix).

What is claimed is:

1. A method for production of bone tissue, comprising the steps of:
   (a) applying undifferentiated mammalian cells on an implant substrate formed from a material selected from the group consisting of metal, calcium phosphate, and polymer, wherein the material is sufficient to allow fixation of the implant substrate at a site of implantation;
   (b) directly contacting the undifferentiated cells with a culture medium for a sufficient time to differentiate the undifferentiated cells and form osteoblasts and wherein said osteoblasts produce an extracellular bone tissue matrix;
   (c) removing the substrate with the bone tissue matrix from the culture medium.

2. A method according to claim 1, wherein said undifferentiated mammalian cells comprise bone marrow cells.

3. A method according to claim 1, wherein said cells comprise autologous cells.

4. A method according to claim 1, wherein step (a) further comprises applying undifferentiated mammalian cells on a substrate at a rate of $10^3$ to $10^6$ cells per $cm^2$.

5. A method according to claim 1, wherein the culture medium in step (b) comprises a conditioned liquid culture medium.

6. A method according to claim 5, wherein the culture medium in step (b) is conditioned by prior exposure to viable marrow cells.

7. A method according to claim 1, wherein the matrix has a thickness of at least 0.5 μm.

8. A method according to claim 1, wherein the substrate is a device selected from the group consisting of a bone filler substance, a load-bearing implant, joint prosthesis, maxillofacial implant and special surgery device.

9. A method of restoring a load-bearing structure in a mammal, including a human, comprising introducing a substrate comprising a coating comprising a continuous matrix produced according to claim 1 as an implant into the site of the structure to be restored.

10. A method according to claim 2, wherein the undifferentiated mammalian cells comprise stromal cells.

11. A method according to claim 7, wherein the matrix has a thickness of between 1 μm to 100 μm.

12. A method according to claim 11, wherein the matrix has a thickness of between 10 μm to 50 μm.

13. A method of claim 1 wherein the matrix comprises a mineralized matrix.

14. A method of claim 1 wherein the matrix comprises a largely non-mineralized matrix.

15. The method of claim 1 wherein the implant substrate is porous.

16. The method of claim 1 wherein the implant substrate is nonporous.

17. A product formed by a method for production of bone tissue, comprising the steps of:
   (a) applying undifferentiated mammalian cells on an implant substrate formed from a material selected from the group consisting of metal, calcium phosphate, and polymer, wherein the material is sufficient to allow fixation of the implant substrate at a site of implantation;
   (b) directly contacting the undifferentiated cells with a culture medium for a sufficient time to differentiate the undifferentiated cells and form osteoblasts and wherein the osteoblasts produce an extracellular bone tissue matrix;
   (c) removing the substrate with the bone tissue matrix from the culture medium.

* * * * *

UNITED STATES PATENT AND TRADEMARK OFFICE
CERTIFICATE OF CORRECTION

PATENT NO. : 6,299,650 B1
DATED : October 9, 2001
INVENTOR(S) : Van Blitterswijk et al.

It is certified that error appears in the above-identified patent and that said Letters Patent is hereby corrected as shown below:

<u>Title page,</u>
Item [30], Foreign Application Priority Data, kindly amend the section as follows:

-- Mar. "3" --1--, 1996 (EP)…………………...96200553
   Sep. 11, 1996 (EP)………………………..96202536 --

Signed and Sealed this

Thirteenth Day of May, 2003

JAMES E. ROGAN
*Director of the United States Patent and Trademark Office*